United States Patent [19]

Hoelderich et al.

[11] Patent Number: 4,806,679

[45] Date of Patent: Feb. 21, 1989

[54] ISOMERIZATION OF DIACYLOXYBUTENES

[75] Inventors: Wolfgang Hoelderich, Frankenthal; Rolf Fischer, Heidelberg; Otto Hertel, Ludwigshafen; Wolf D. Mross, Frankenthal; Hans-Martin Weitz, Bad Durkheim, all of Fed. Rep. of Germany

[73] Assignee: BASF Aktiengesellschaft, Ludwigshafen, Fed. Rep. of Germany

[21] Appl. No.: 633,279

[22] Filed: Jul. 23, 1984

[30] Foreign Application Priority Data

Jul. 23, 1983 [DE] Fed. Rep. of Germany ....... 3326668

[51] Int. Cl.$^4$ .................... C07C 67/293; C07C 69/16; C07C 69/28
[52] U.S. Cl. .................................. 560/262; 560/261; 562/607
[58] Field of Search ......................................... 560/262

[56] References Cited

U.S. PATENT DOCUMENTS

| | | | |
|---|---|---|---|
| 3,830,833 | 8/1974 | Mabuchi et al. | 560/262 |
| 4,182,901 | 1/1980 | Fozzard et al. | 560/262 |
| 4,465,853 | 8/1984 | Yoshida et al. | 560/262 |
| 4,468,475 | 8/1984 | Kuehl | 502/71 |

FOREIGN PATENT DOCUMENTS

| | | |
|---|---|---|
| 2134115 | 1/1972 | Fed. Rep. of Germany . |
| 2454768 | 5/1976 | Fed. Rep. of Germany . |
| 2736695 | 3/1979 | Fed. Rep. of Germany . |
| 3022288 | 12/1980 | Fed. Rep. of Germany . |
| 50-126611 | 10/1975 | Japan . |
| 1519038 | 7/1978 | United Kingdom . |
| 2051805 | 1/1981 | United Kingdom . |

*Primary Examiner*—Vivian Garner
*Attorney, Agent, or Firm*—Keil & Weinkauf

[57] ABSTRACT

1,4-Diacyloxybut-2-enes and 3,4-diacyloxybut-1-enes are converted into one another in the gas phase or liquid phase at from 100° to 350° C. under atmospheric or superatmospheric pressure in the presence of a zeolite as a catalyst.

5 Claims, No Drawings

ISOMERIZATION OF DIACYLOXYBUTENES

The present invention relates to a process for converting 1,4-diacyloxybut-2-enes (I) and 3,4-diacyloxybut-1-enes (II) into one another in the gas phase or liquid phase in the presence of a zeolite.

Diacyloxybutenes of the formulae I and II are useful intermediates. For example, 1,4-diacetoxybut-2-ene can be converted into butane-1,4-diol and tetrahydrofuran by hydrogenation and hydrolysis. By means of hydroformylation and elimination of one mole of acetic acid, 3,4-diacyloxybut-1-enes can be converted to trans-2-methyl-4-acetoxybut-2-enal, which is a component for the synthesis of terpenes, e.g., vitamin A acetate.

Mixtures of diacyloxybutenes of the formulae I and II can be prepared by reacting butadiene or a substituted 1,3-diene with a carboxylic acid and oxygen in the presence of a palladium-containing or platinum-containing catalyst.

It has been disclosed that 3,4-diacyloxybut-1-enes and 1,4-diacyloxybut-2-enes can be converted into one another by heating in the liquid phase in the presence of a homogeneous solution of a metal compound. This is done using, for example, selenium dioxide in the presence of lithium acetate, acetic acid and acetic anhydride (U.S. Pat. No. 4,182,901). It is also possible to employ palladium or platinum compounds, such as platinum halides or palladium halides, in the presence of oxygen (German Laid-Open Applications DOS 2,454,768 and DOS 2,134,115) or oxygen and chlorine (German Laid-Open Application DOS 2,736,695).

The stated isomerization has also been carried out using heterogeneous catalysts in the liquid phase, for example cation exchangers such as Amberlite 200 C (German Laid-Open Application No. 3,022,288).

An example of a heterogeneous catalyst which has been used in the gas phase is γ-alumina (Japanese Application No. 50126 611).

It is also known that zeolites can be used for the skeletal isomerization of paraffins, olefins and alkyl-substituted aromatics. For example, European Patent 812 describes the isomerization of xylene over ZSM5 zeolites as a preferred method of preparing p-xylene from a mixture of $C_8$-aromatics.

In the case of homogeneous catalysts used in the liquid phase, the conventional processes for converting 3,4-diacyloxybut-1-enes and 1,4-diacyloxybut-2-enes into one another have the disadvantages that the catalyst has to be separated off after the reaction and recycled to the reaction zone, and may have to be regenerated. In the case of the heterogeneous catalysts employed in the gas phase, the selectivity (e.g., 68% for γ-$Al_2O_3$ at 40% conversion) and the catalyst life (Pd on active carbon in the presence of hydrogen halides) present problems.

We have found that a 1,4-diacyloxybut-2-ene of the formula

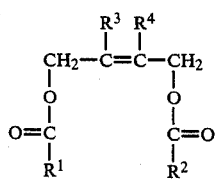

and a 3,4-diacyloxybut-1-ene of the formula

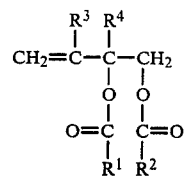

where $R^1$ and $R^2$ can be identical or different and are each hydrogen or alkyl of 1 to 3 carbon atoms, and $R^3$ and $R^4$ can be identical or different and are each hydrogen or methyl, can be particularly advantageously converted into one another if the reaction is carried out in the gas phase or liquid phase in the presence of a zeolite as a catalyst.

In the case of cis- and trans-1,4-diacetoxybut-2-ene and 3,4-diacetoxybut-1-ene, the conversion of the diacyloxybutenes I and II into one another can be represented by the following formulae:

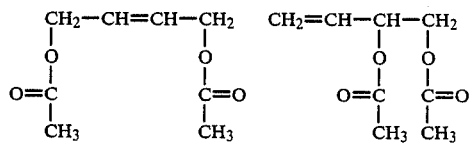

Examples of diacyloxybutenes I and II, which can be used in the form of pure compounds or as mixtures, are cis- and trans-1,4-diacetoxybut-2-ene, 3,4-diacetoxybut-1-ene, 1,4-diformyloxybut-2-ene, 3,4-diformyloxybut-1-ene, 1,4-diacetoxy-2-methylbut-2-ene, 1,4-dipropionyloxybut-2-ene, 3,4-dipropionyloxybut-1-ene, 1,4-diacetoxy-2,3-dimethylbut-2-ene, 3,4-diacetoxy-3-methylbut-1-ene, 3,4-diacetoxy-2-methylbut-1-ene and 3,4-diacetoxy-2,3-dimethylbut-1-ene. Cis- and trans-1,4-diacetoxybut-2-ene and 3,4-diacetoxybut-1-ene are particularly preferred.

Zeolites are employed as catalysts for the isomerization of diacyloxybutenes. Zeolites are crystalline aluminosilicates which possess a highly ordered structure with a rigid three-dimensional network of $SiO_4$- and $AlO_4$-tetrahedra linked via common oxygen atoms. The ratio of Si and Al atoms to oxygen is 1:2. The electrovalency of the aluminum-containing tetrahedra is balanced by the inclusion of cations in the crystal, for example, an alkali metal ion or hydrogen ion. Cation exchange is possible. The spaces between the tetrahedra are occupied by water molecules before dehydration is effected by drying or calcination.

Crystalline compounds which have a zeolite structure and in which the zeolite framework contains trivalent elements such as B, Ga, Fe or Cr instead of the aluminum, or tetravalent elements such as Ge instead of the silicon, also exist.

Preferably used catalysts for the isomerization of diacyloxybutenes are zeolites of the pentasil type.

These zeolites can have different chemical compositions. Aluminosilicate, borosilicate, iron silicate, gallium silicate, chromium silicate, arsenosilicate or bismuth silicate zeolites or mixtures of these, and aluminogermanate, borogermanate, gallium germanate or iron germanate zeolites or mixtures of these, can be used.

The aluminosilicate and borosilicate zeolites are particularly useful for the claimed isomerization. The aluminosilicate zeolite is prepared from an aluminum compound, preferably Al(OH)$_3$ or Al$_2$(SO$_4$)$_3$, and a silicon component, preferably highly disperse silicon dioxide, in an aqueous solution of an amine, in particular a solution of hexane-1,6-diamine, propane-1,3-diamine or triethylenetetramine, with or without the addition of an alkali or alkaline earth metal, at from 100° to 220° C. under autogenous pressure. Depending on the amounts of starting materials chosen, the resulting aluminosilicate zeolites have an SiO$_2$/Al$_2$O$_3$ ratio of from 10 to 40,000.

Aluminosilicate zeolites of this type can also be synthesized in an ester medium, such as diethylene glycol dimethyl ether, in an alcoholic medium, such as methanol or butane-1,4-diol, or simply in water.

The borosilicate zeolite is synthesized by reacting a boron compound, e.g., H$_3$BO$_3$, with a silicon compound, preferably highly disperse silicon dioxide, in an aqueous solution of an amine, in particular a solution of hexane-1,6-diamine, propane-1,3-diamine or triethylenetetramine, with or without the addition of an alkali or alkaline earth metal, at from 90° to 170° C. under autogenous pressure.

Borosilicate zeolites of this type can also be obtained if the reaction is carried out not in an aqueous solution of an amine but in solution in an ether, eg. diethylene glycol dimethyl ether, or in alkaline solution.

The aluminosilicate and borosilicate zeolites prepared in this manner are isolated, dried at from 100° to 160° C., preferably 110° C., and calcined at from 450° to 550° C., preferably 500° C., after which they are molded together with a binder in a weight ratio of from 90:10 to 40:60 to give extrudates or tablets. Suitable binders are various aluminas, preferably boehmite, amorphous aluminosilicates having an SiO$_2$/Al$_2$O$_3$ ratio of from 25:75 to 95:5, preferably 75:25, silicon dioxide, preferably disperse SiO$_2$, mixtures of highly disperse SiO$_2$ and highly disperse Al$_2$O$_3$, highly disperse TiO$_2$, and clay. After the molding step, the extrudates or pellets are dried at 110° C. for 16 hours and calcined at 500° C. for 16 hours.

In a particular embodiment, the aliminosilicate or borosilicate zeolite which has been isolated is molded immediately after the drying step and is subjected to calcination only after the molding procedure.

Aluminosilicate zeolites of the Y type which have been prepared from silicasol (29% SiO$_2$) and sodium aluminate in an aqueous medium can also be used. These aluminosilicate zeolites can likewise be molded together with a binder before being used.

When the zeolite catalysts have become deactivated due to coking during the reaction claimed above, the catalysts can be regenerated in a simple manner by burning off the coke deposit in air or an air/N$_2$ mixture at from 400° to 550° C., preferably 500° C.; as a result of this procedure, the catalyst regains its initial activity.

In order to increase the selectivity, the catalyst life and the number of regenerations, these zeolite catalysts can be modified in different ways.

In one possible method of modifying the catalysts, the unmolded zeolites or the zeolite molding are doped or subjected to an ion exchange reaction with an alkali metal, e.g., Na, an alkaline earth metal, e.g., Ca or Mg, an earth metal, e.g., B or Tl, a transition metal, e.g., Mn, Fe, Mo, Cu or Zn, or a rare earth metal, e.g., La or Ce.

In a particular embodiment, the pentasil zeolite moldings are initially taken in an ascending tube and, for example, a halide or a nitrate of one of the metals described above is passed over at from 20° to 100° C. Ion exchange of this type can be carried out on, for example, the hydrogen, ammonium or alkali metal form of the zeolite.

Another possible method of introducing the metal onto the zeolite comprises impregnating the zeolite material with, for example, a halide, a nitrate or an oxide of one of the metals described above, in aqueous or alcoholic solution.

Both ion exchange and impregnation are followed by a drying step, and, if desired, further calcination may be carried out.

Metal-doped zeolites can be after-treated with hydrogen. Another possible method of modification comprises treating the zeolite material, either in molded or unmolded form, with an acid, such as hydrochloric acid, hydroflouric acid or phosphoric acid.

In a particular embodiment, the zeolite powder, before being molded, is refluxed with 0.001–2N, preferably 0.05–0.5N, hydrofluoric acid for from 1 to 3 hours. The product is then filtered off, washed, dried at from 100° to 160° C. and then calcined at from 450° to 600° C.

In another particular embodiment, the zeolite is molded together with a binder, and the moldings are then treated with HCl. In this procedure, the zeolite is treated in a 3–25, in particular 12–20, % strength hydrochloric acid for from 1 to 3 hours at from 60° to 80° C., and the product is then washed, dried at from 100° to 160° C. and calcined at from 450° to 600° C. By means of partial precoking, it is also possible to adjust the activity of the catalyst to achieve optimum selectivity with respect to the desired product.

The catalysts described here are employed alternatively in the form of 2–4 mm extrudates, tablets having a diameter of 3 to 5 mm or powders having a particle size of 0.1 to 0.5 mm.

The reaction conditions chosen for the isomerization in the gas phase are 180°–400° C., preferably 250°–300° C., and a WHSV of from 0.1 to 10 h$^{-1}$ (g of diacyloxybutene per g of catalyst per hour).

The isomerization of the diacyloxybutenes can also be carried out in the liquid phase at from 100° to 170° C.

The Examples which follow illustrate the invention.

EXAMPLE 1

Catalyst A

The aluminosilicate zeolite of the pentasil type is synthesized from 65 g of SiO$_2$ (Aerosil 200) and 20.3 g of Al$_2$(SO$_4$)$_3$.18H$_2$O in 1 kg of an aqueous hexane-1,6-diamine solution (weight ratio 50:50) in a stirred autoclave under hydrothermal conditions, under autogenous pressure and at 150° C. The crystalline product is filtered off, washed, dried at 110° C. for 24 hours and then calcined at 500° C. for 24 hours. This aluminosilicate zeolite, which contains 91.6% by weight of SiO$_2$ and 4.6% by weight of Al$_2$O$_3$, is mixed with boehmite in a weight ratio of 60:40, the mixture is converted to 2 mm extrudates and the latter are dired at 110° C. for 16 hours and calcined at 500° C. for 24 hours.

Catalyst B

Catalyst B is prepared as described for catalyst A, except that the aqueous hexane-1,6-diamine solution is replaced by an aqueous propane-1,3-diamine solution of the same concentration. This aluminosilicate zeolite is composed of 90% by weight of SiO$_2$ and 3.5% by weight of Al$_2$O$_3$. The crystallite size is from 10 to 12 μm.

Catalyst C

Catalyst C is prepared similarly to catalyst B. The aluminosilicate zeolite is composed of 90.6% by weight of $SiO_2$ and 3.9% by weight of $Al_2O_3$, and its crystallite size is from 0.1 to 0.5 μm.

Catalyst D

The boron zeolite of the pentasil type is prepared from 64 g of $SiO_2$ (Aerosil 200), 12.2 g of $H_3BO_3$ and 800 g of an aqueous hexane-1,6-diamine solution (weight ratio 50:50) in a stirred autoclave at 170° C. under autogenous pressure, in a hydrothermal synthesis. The crystalline product is filtered off, washed, dried at 100° C. for 24 hours and then calcined at 500° C. for 24 hours. This borosilicate zeolite, which is composed of 94.2% by weight of $SiO_2$ and 2.32% by weight of $B_2O_3$, is molded together with boehmite in a weight ratio of 60:40 to give 2 mm extrudates, and the latter are dried at 110° C. for 16 hours and calcined at 500° C. for 24 hours.

Catalyst E

Catalyst E is prepared from catalyst A by impregnating the latter with 0.88 molar $Cu(NO_3)_2.2H_2O$.

Catalyst F

Catalyst F is prepared by refluxing catalyst C with 1N hydrochloric acid for 1 hour. The product is washed with water and is then dried at 100° C. for 16 hours and calcined at 500° C. for 5 hours.

EXPERIMENTS 1 TO 10

Experiments 1 to 10 illustrate the use of the catalysts described above for converting 1,4-diacyloxybut-2-enes and 3,4-diacyloxybut-1-enes into one another in the gas phase (Table). Examples of low boiling by-products of the reaction are acetic acid and butadienyl acetates.

The starting material of the formula I contains 92.3% by weight of trans-1,4-diacetoxybutene and 5.9% by weight of cis-1,4-diacetoxybutene.

The starting material of the formula II is composed of 99.6% by weight of 3,4-diacetoxybutene and 0.4% by weight of trans- and cis-1,4-diacetoxybutene.

The experiments are carried out in a reaction tube under isothermal conditions. The starting material is vaporized in a preheating zone before it comes into contact with the catalyst. The products are condensed, and are identified by analysis by gas chromatography.

EXAMPLE 2

This Example describes the procedure for converting 1,4-diacetoxybut-2-ene to 3,4-diacetoxybutene in the liquid phase in the presence of catalyst A. A heated quartz tube having a diameter of 4 cm and a length of 40 cm is charged with 184 g of catalyst A, and 0.11 liter/hour of 1,4-diacetoxybut-2-ene is pumped through this reaction tube at 228° C.

A residence time of 2.5 hours gives a reaction mixture which contains 77% by weight of 1,4-diacetoxybut-2-ene, 13% by weight of 3,4-diacetoxybutene and 10% by weight of by-products.

We claim:

1. A process for converting diacyloxybutenes into one another in the gas phase or liquid phase at from 100° to 350° C. under atmospheric or superatmospheric pressure in the presence of a catalyst, wherein a 1,4-diacyloxybut-2-ene of the formula I

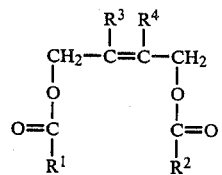

and a 3,4-diacyloxybut-1-ene of the formula II

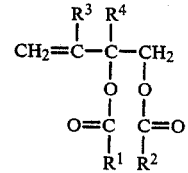

where $R^1$ and $R^2$ can be identical or different and are each hydrogen or alkyl of 1 to 3 carbon atoms, and $R^3$ and $R^4$ can be identical or different and are each hydrogen or methyl, are converted into one another in the presence of a zeolite catalyst.

2. A process as claimed in claim 1, wherein the catalyst used is a zeolite of the pentasil type.

3. A process as claimed in claim 1, wherein the catalyst used is an aluminosilicate zeolite.

4. A process as claimed in claim 1, wherein the catalyst used is a borosilicate zeolite.

5. A process as claimed in claim 1, wherein the catalyst used is an aluminosilicate zeolite of the Y type.

* * * * *

TABLE

| Experiment | 1 | 2 | 3 | 4 | 5 |
|---|---|---|---|---|---|
| Catalyst | A | A | E | B | C |
| Starting material | 1,4-DAOB | 1,4-DAOB | 1,4-DAOB | 1,4-DAOB | 1,4-DAOB |
| Temperature | 300° C. | 300° C. | 300° C. | 300° C. | 300° C. |
| WHSV | $6.2\ h^{-1}$ | $3.1\ h^{-1}$ | $6.2\ h^{-1}$ | $6.2\ h^{-1}$ | $6.2\ h^{-1}$ |
| Products, % by weight | | | | | |
| trans-1,4 BEDA | 53.2 | 38.3 | 55.2 | 64.2 | 60.1 |
| cis-1,4 BEDA | 5.3 | 5.4 | 7.7 | 5.5 | 5.0 |
| 3,4 BEDA | 26.3 | 37.0 | 21.7 | 16.2 | 17.0 |
| By-products | 12.2 | 15.9 | 13.8 | 11.2 | 14.0 |
| Experiment | 6 | 7 | 8 | 9 | 10 |
| Catalyst | F | D | D | D | E |
| Starting material | 1,4-DAOB | 1,4-DAOB | 1,4-DAOB | 3,4-DAOB | 3,4-DAOB |
| Temperature | 300° C. | 300° C. | 300° C. | 200° C. | 300° C. |
| WHSV | $3.1\ h^{-1}$ | $6.2\ h^{-1}$ | $3.1\ h^{-1}$ | $6.2\ h^{-1}$ | $6.2\ h^{-1}$ |
| Products, % by weight | | | | | |
| trans-1,4 BEDA | 34.6 | 29.5 | 42.2 | 18.4 | 11.3 |
| cis-1,4 BEDA | 5.7 | 5.8 | 6.0 | 1.55 | 1.5 |
| 3,4 BEDA | 36.2 | 25.5 | 26.6 | 75.3 | 82.1 |
| By-products | 21.4 | 34.6 | 22.0 | 4.9 | 4.8 |